(12) United States Patent
Edwards

(10) Patent No.: US 6,209,337 B1
(45) Date of Patent: Apr. 3, 2001

(54) WATER COLLECTION AND PURIFICATION SYSTEM

(76) Inventor: William F. Edwards, 109 Seasons Dr., Raleigh, NC (US) 27614-8421

( * ) Notice: Subject to any disclaimer, the term of this patent is extended or adjusted under 35 U.S.C. 154(b) by 0 days.

(21) Appl. No.: 09/156,236

(22) Filed: Sep. 18, 1998

Related U.S. Application Data

(60) Provisional application No. 60/059,567, filed on Sep. 19, 1997.

(51) Int. Cl.⁷ ..................................................... F25D 21/00
(52) U.S. Cl. .................................. 62/272; 62/93; 62/264; 62/285
(58) Field of Search ............................... 62/93, 264, 272, 62/285

(56) References Cited

U.S. PATENT DOCUMENTS

| | | |
|---|---|---|
| 3,035,418 | 5/1962 | Wright . |
| 4,255,937 | 3/1981 | Ehrlich . |
| 5,149,446 | 9/1992 | Reidy . |
| 5,203,989 | 4/1993 | Reidy . |
| 5,259,203 | 11/1993 | Engel et al. . |
| 5,301,516 | 4/1994 | Pointdexter . |
| 5,366,705 | 11/1994 | Reidy . |
| 5,517,829 | 5/1996 | Michael . |
| 5,701,749 | * 12/1997 | Zakryk ...................................... 62/93 |
| 5,729,981 | * 3/1998 | Markus et al. ........................... 62/3.4 |
| 5,768,905 | * 6/1998 | Oh ........................................... 62/264 |

* cited by examiner

*Primary Examiner*—William Doerrler
*Assistant Examiner*—Mark Shulman
(74) *Attorney, Agent, or Firm*—Kenneth L. Tolar

(57) ABSTRACT

A portable water purification and collection system includes a cabinet member having an interior chamber defined by a plurality of side walls, one of which has a vent thereon. Received within the interior chamber and adjacent the vent is a fan for inducing air flow from the atmosphere to the cabinet interior. Between the fan and the vent is an electrostatic air filter for removing particulates from the air as well as a condenser for producing condensate therefrom. The resulting condensate drips into a collection reservoir and then to an ultraviolet light unit that destroys microorganisms within the condensate. From the ultraviolet light unit, the condensate flows to a main reservoir from which it may be dispensed to an external container via a spigot mounted to a cabinet side wall.

14 Claims, 4 Drawing Sheets

FIG.4

WITH THE HYDRO-RETRIEVER IN THE PROTOTYPE STAGE, THE BELOW DATA WAS DEVELOPED.

| TIME HOURS | VOLTAGE | AMP | WATT HOURS | kWh | $/kWh HOURS | GAL. | LITERS | $/GAL. | TEMP-D | TEMP-W | %-H | COMMENT |
|---|---|---|---|---|---|---|---|---|---|---|---|---|
| 1.0 | 115 | 3.1 | 356.5 | 0.3565 | 0.09 | 0.050 | 0.189 | 0.640 | 74° F | 60° F | 42% | RAIN DAY |
| 2.0 | 115 | 3.1 | 713.0 | 0.7130 | 0.09 | 0.1560 | 0.591 | 0.410 | 86° F | 60° F | 39% | CLEAR DAY |
| 3.0 | 115 | 3.1 | 1069.5 | 1.0695 | 0.09 | 0.3125 | 1.180 | 0.40 | 73° F | 68° F | 60% | CLEAR DAY |
| 4.0 | 115 | 3.1 | 1426.0 | 1.4260 | 0.09 | 0.2960 | 1.120 | 0.43 | 82° F | 70° F | 55% | CLEAR DAY |
| 5.0 | 115 | 3.1 | 1782.5 | 1.7825 | 0.09 | 0.2500 | 0.945 | 0.64 | 76° F | 60° F | 38% | RAIN DAY |
| 6.0 | 115 | 3.1 | 2139.0 | 2.1390 | 0.09 | 0.3910 | 1.480 | 0.49 | 82° F | 68° F | 42% | CLEAR DAY |
| 7.0 | 115 | 3.1 | 2495.5 | 2.4950 | 0.09 | 0.4690 | 1.770 | 0.48 | 78° F | 65° F | 46% | CLEAR DAY |
| 8.8 | 115 | 3.1 | 3137.2 | 3.1372 | 0.09 | 0.5630 | 2.130 | 0.50 | 80° F | 78° F | 91% | CLEAR DAY |

| 24 | 115 | 3.1 | 8556 | 8.556 | 0.09 | 1.875 | 7.088 | 0.41 | 88° F | 86° F | 92% | THEORETICAL |

IT WAS CONCLUDED BY EXTRAPOLATION, THAT THE AMOUNT OF WATER PRODUCED COULD BE INCREASED BY INCREASING THE AREA OF THE COOLING COIL.

| | | | |
|---|---|---|---|
| TIME HOURS | – HOURS | $/kWh | – DOLLARS PER KILOWATT HOUR |
| VOLTAGE | – VOLTAGE | GAL | – GALLONS |
| AMP | – AMPERAGE | LITER | – LITER |
| WATT-HRS | – WATTAGE HOURS | $/GAL | – DOLLAR PER GALLON |
| kWh | – KILOWATT HOURS | TEMP-W | – WET THERMOMETER READER |
| TEMP-D | – DRY THERMOMETER READING | H% | – PERCENT HUMIDITY |

WATER COLLECTION AND PURIFICATION SYSTEM

BACKGROUND OF THE INVENTION

This application is entitled to the benefit of the filing date of provisional application No. 60/059,567 filed on Sep. 19, 1997. The present invention relates to a water purification system for extracting and purifying water from ambient air.

DESCRIPTION OF THE PRIOR ART

Various processes for purifying water exist in the prior art. Examples of such processes include filtration, anion/cation exchange, distillation and reverse osmosis. Each process is often supplemented with chlorination, oxidation, ultraviolet radiation and similar treatment methods. However, each of the aforementioned processes has several disadvantages. Filtering employs a filter medium that must be cleaned or periodically replaced which is expensive and laborious. Ion exchange resin is susceptible to destruction by other water treatment chemicals especially chlorine. Reverse osmosis is effective in removing most contaminants but the process requires a significant amount of raw input water to produce a predetermined amount of purified water.

Distillation involves boiling water and condensing the steam produced thereby. Because most of the dissolved solids remain with the liquid, the condensed steam is essentially pure. However, many volatile organics such as pesticides will vaporize with the steam and will be condensed therewith. Additionally, distillation requires a boiler or a similar steam producing device which is expensive to operate and maintain.

The present invention overcomes each of the disadvantages enumerated above by providing a device that condenses moisture from ambient air and collects such moisture within a storage reservoir. The storage reservoir includes a dispensing spigot in fluid communication therewith allowing the collected condensate to be dispensed into an external container. Although similar devices have been developed, the present invention includes an ultraviolet light unit having a sight port and a light cleaning means to ensure proper and efficient operation of the device.

SUMMARY OF THE INVENTION

The present invention relates to a device for conveniently purifying and collecting water vapor entrained within ambient air. The device comprises a cabinet member having an air vent on a side wall thereof through which ambient air is delivered to the cabinet interior. Within the cabinet is an air intake fan, a condenser, a collection reservoir, a main reservoir, an ultraviolet light unit and a compressor. Ambient air is drawn through a filtering device and delivered to the condenser wherein moisture entrapped within the ambient air is condensed. The resulting moisture drips into the collection reservoir, is sterilized in an ultraviolet unit and is transferred to the main storage reservoir from which it may be selectively dispensed to an external container. It is therefore an object of the present invention to provide a portable water purification and collection device that provides a complete, multi stage treatment process for removing particulates, organics and inorganics from a water source.

It is yet another object of the present invention to provide a water purification and collection device that provides an inexpensive means for purifying a water source.

It is yet another object of the present invention to provide a water purification and collection device that produces sterile, purified water from ambient air. Other objects, features and advantages of the present invention will become readily apparent from the following detailed description of the preferred embodiment when considered with the attached drawings and the appended claims.

BRIEF DESCRIPTION OF THE DRAWINGS

FIG. 4 correlates operational data for the present invention to various ambient conditions.

DESCRIPTION OF THE PREFERRED EMBODIMENT

Figure 1:
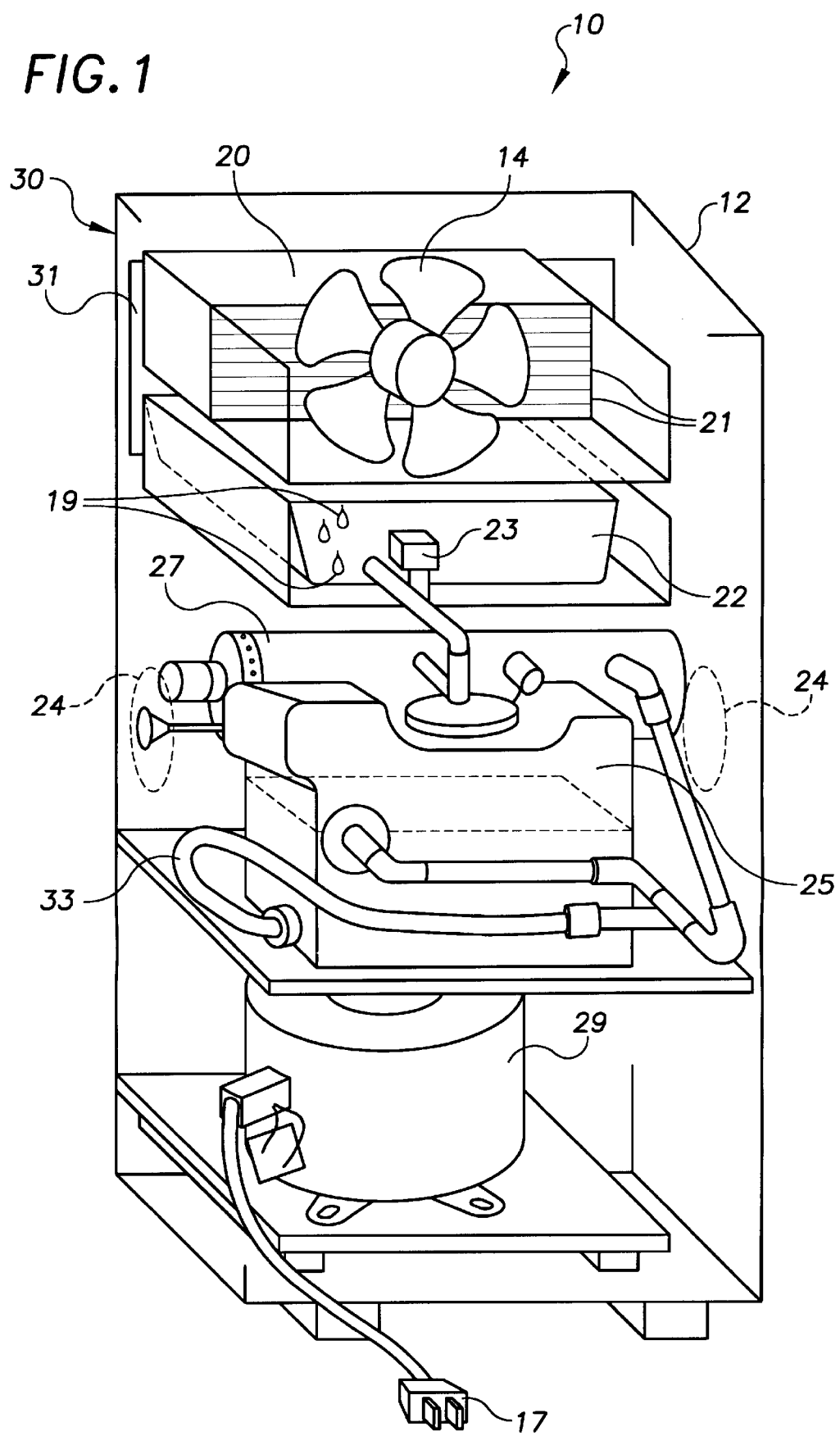
FIG. 1 depicts the internal components according to the present invention.
Figure 2:
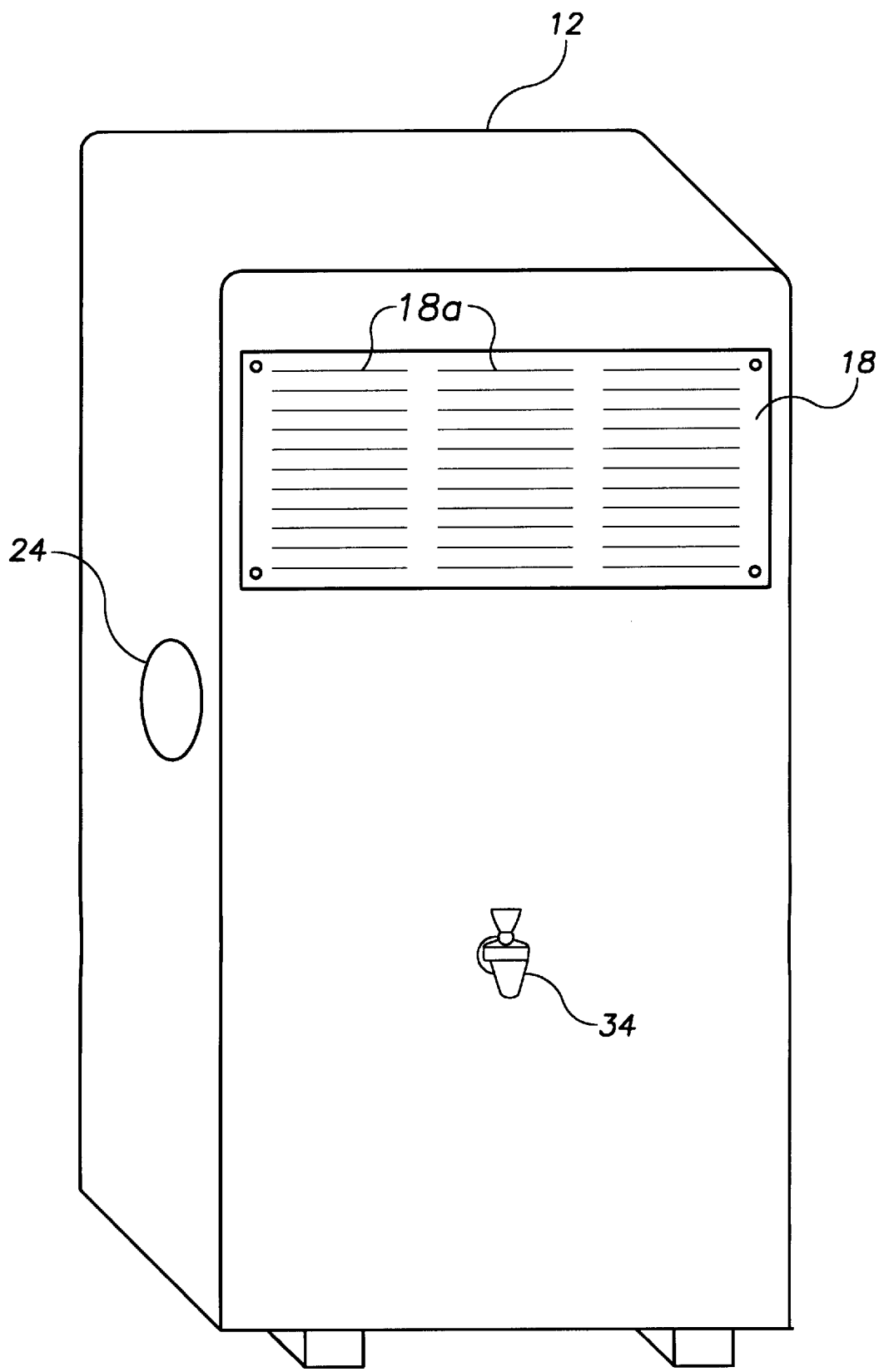
FIG. 2 depicts a front exterior view of the cabinet according to the present invention.

Referring now to FIGS. 1 through 4, the present invention relates to a water collection and purification device, indicated generally at 10. The device includes a cabinet member 12 having a plurality of side walls and an interior chamber. One of the side walls may be removable or pivotable to provide selective access to the interior chamber components that are described in more detail below. A first side wall includes a plurality of louvers 18A formed on a vent cover 18 for providing ambient air to the cabinet interior chamber. The device also includes a plurality of exhaust ducts 24 on one or more side walls thereof for allowing air to flow from the cabinet interior to the atmosphere.

Received within the cabinet interior chamber and proximal the vent is a fan 14 for inducing air flow from the atmosphere to the interior chamber. Between the fan and the vent is an electrostatic filter 31 for removing various particulates from the incoming air. The electrostatic filter 31 is a conventional item and includes fibrous, electrically charged filter media for attracting oppositely charged particulates entrained within the ambient air. The filter media is sufficiently charged to also attract substantially neutral particles to ensure that substantially all particulate matter within the incoming air is removed prior to condensation being produced.

Disposed between the filter and fan is a condenser unit 20 having refrigerant coils therein 21 across which ambient air is circulated by the fan. A refrigerant compressor 29 is received within the cabinet and is in fluid communication with the condenser coils for circulating a refrigerant therethrough. Accordingly, the compressor compresses and circulates the refrigerant through the coils to cool ambient air flowing thereacross to a temperature sufficient to produce condensate. The resulting condensate drips into a collection reservoir 22 and ultimately to a UV light unit 27 via conduit 23.

Figure 3:
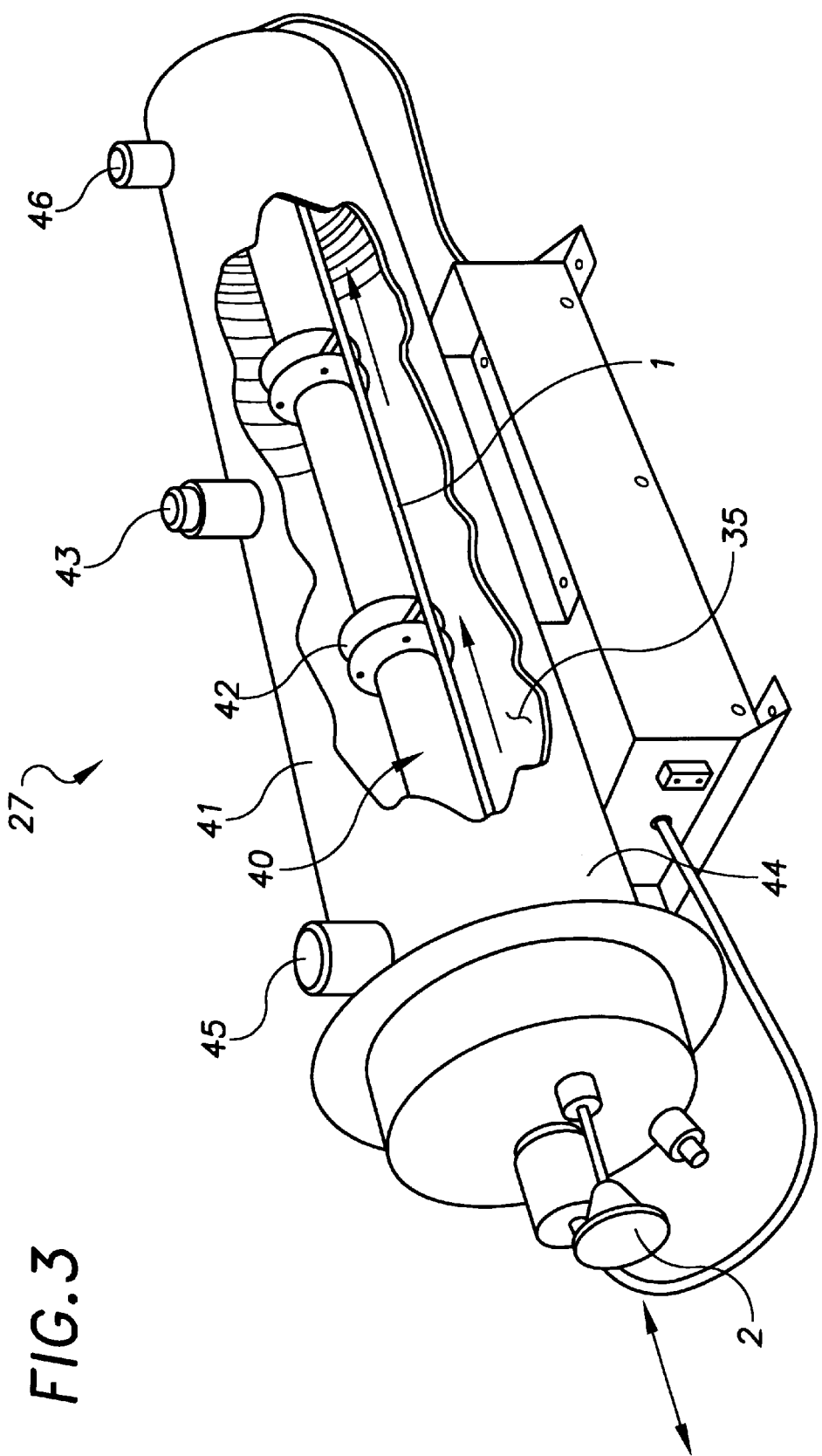
FIG. 3 depicts the ultraviolet unit according to the present invention.

Referring now to FIG. 3, the conventional ultraviolet light unit 27 according to the present invention is depicted in more detail. The unit includes a hollow, substantially cylindrical housing 44 having a condensate input 45 and condensate output 46. The condensate enters the housing from the collection reservoir and flows through an annular space 35 formed between a quartz sleeve 40 and the UV light unit housing outer wall 41. The quartz sleeve includes a germicidal lamp therein for emitting ultraviolet rays that immediately destroy microorganisms exposed thereto. Annular discs 42 surround the quartz sleeve for inducing turbulent condensate flow through the housing to ensure that the microbiological organisms are thoroughly exposed to ultraviolet radiation. A sight port 43 on the housing enables visual observation of the lamp operation and condition. An extendable and retractable rod 1 is attached to the annular discs and includes a knob 2 on an end thereof that extends from an end of the ultraviolet light unit housing. By reciprocating the knob towards and away from the housing, a user may dislodge debris from the quartz sleeve without disassembling the housing or otherwise interrupting the purification process. The above described device is conventional and may include the product sold under the mane SANITRON ™, ATLANTIC ULTRAVIOLET or a similar equivalent.

Upon exiting the ultraviolet light unit, the condensate flows to a main reservoir 25. The main reservoir 25 includes a discharge pipe 33 in fluid communication with a spigot 34 mounted exteriorly of the cabinet, preferably on a side wall thereof, to dispense the purified condensate to an external container. The main reservoir may also include a float valve mechanism (not pictured) for disabling flow to the spigot upon the level in the reservoir diminishing below a predetermined level.

FIG. 4 provides a chart interrelating various ambient conditions to the approximate number of hours required to produce a predetermined volume of water. Also included is the approximate energy cost to produce a given volume of water as calculated at an assumed cost of nine cents per kilowatt hour. Accordingly, the system according to the present invention can be operated at optimal temperatures and/or humidity to minimize associated energy costs and to increase the efficiency of the process. Accordingly, conventional automatic temperature and humidity sensing controls may be electrically integrated with the system to automatically operate the various components only during optimal conditions. The device may also include a plurality of photo voltaic cells mounted on the cabinet or in a remote location to provide power to the various components via a light source.

The present invention is not to be limited to the exact details of construction and arrangement of parts shown and described. In addition, the size, shape and materials of construction may be varied without departing from the spirit of the present invention.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

What is claimed is:

1. A portable water collection and purification system for producing purified water from ambient air, the system comprising:
    a cabinet member having an interior chamber;
    an air circulation means received within said cabinet member for inducing air flow from the atmosphere to said cabinet interior chamber;
    a condenser means received within said interior chamber for cooling ambient air to a temperature sufficient to induce moisture condensation therefrom;
    a first reservoir means adjacent said condenser means for receiving condensate produced by said condenser means;
    a second reservoir means in fluid communication with said sterilizing means for receiving said condensate therefrom;
    an ultraviolet light unit in fluid communication with said first reservoir means, said unit including a hollow housing having an ultraviolet light source encompassed by a quartz sleeve and a sight port for allowing a user to observe said light source, said sleeve and light source received within said housing, the space between said light source and said housing defining a flow path for said condensate whereby microorganisms within said condensate are exposed to ultraviolet light.

2. A device according to claim 1 wherein said condenser means includes a plurality of refrigerant coils in fluid communication with a compressor that circulates a refrigerant through said coils to condense water vapor entrained within ambient air.

3. A device according to claim 1 further comprising a dispensing means mounted exteriorly of said housing and in fluid communication with said second reservoir means for dispensing condensate from said second reservoir means to an external container.

4. A device according to claim 1 further comprising means for providing electricity to said compressor means, said condenser means and said air circulation means.

5. A device according to claim 1 further comprising:
    a filtering means received within said interior chamber for removing particulates from ambient air.

6. A device according to claim 1 wherein said cabinet member further comprises a plurality of side walls with a vent on one of said side walls.

7. A device according to claim 1 wherein said air circulation means comprises a fan.

8. A device according to claim 6 wherein said housing further comprises an exhaust duct on at least one of said side walls through which air flows from the interior chamber to the atmosphere.

9. A device according to claim 1 wherein said light source includes a plurality of annular discs surrounding the quartz sleeve for inducing turbulent flow of said condensate.

10. A device according to claim 9 wherein said discs have an elongated rod attached thereto, said rod having an end extending from said housing which is grasped and reciprocated to dislodge debris from said sleeve.

11. A device according to claim 4 wherein said means for providing electricity to the compressor means, condenser means and air circulation means comprises a plurality of photo voltaic cells disposed on said housing, each cell electrically connected to said compressor means, said condenser means and said air circulation means.

12. A portable water collection and purification system for producing purified water from ambient air, the system comprising:
    a cabinet member having an interior chamber;
    an air circulation means received within said cabinet member for inducing air flow from the atmosphere to said cabinet interior chamber;
    a condenser means received within said interior chamber for cooling ambient air to a temperature sufficient to induce moisture condensation therefrom;
    a first reservoir means adjacent said condenser means for receiving condensate produced by said condenser means;
    a second reservoir means in fluid communication with said sterilizing means for receiving said condensate therefrom;

an ultraviolet light unit in fluid communication with said first reservoir means, said unit including a hollow housing having an ultraviolet light source encompassed by a quartz sleeve, said sleeve and light source received within said housing, the space between said light source and said housing defining a flow path for said condensate whereby microorganisms within said condensate are exposed to ultraviolet light;

a plurality of annular discs surrounding the quartz sleeve for inducing turbulent flow of said condensate.

13. A device according to claim 12 wherein said discs have an elongated rod attached thereto, said rod having an end extending from said housing which is grasped and reciprocated to dislodge debris from said sleeve.

14. A portable water collection and purification system for producing purified water from ambient air, the system comprising:

a cabinet member having an interior chamber;

an air circulation means received within said cabinet member for inducing air flow from the atmosphere to said cabinet interior chamber;

a condenser means received within said interior chamber for cooling ambient air to a temperature sufficient to induce moisture condensation therefrom;

a first reservoir means adjacent said condenser means for receiving condensate produced by said condenser means;

a second reservoir means in fluid communication with said sterilizing means for receiving condensate therefrom;

an ultraviolet light unit in fluid communication with said first reservoir means, said unit including a hollow housing having an ultraviolet light source encompassed by a quartz sleeve, said sleeve and light source received within said housing, the space between said light source and said housing defining a flow path for said condensate whereby microorganisms within said condensate are exposed to ultraviolet light;

means for providing electricity to said compressor means, said condenser means and said air circulation means wherein said means for providing electricity to the compressor means, condenser means and air circulation means comprises a plurality of photo voltaic cells disposed on said housing, each cell electrically connected to said compressor means, said condenser means and said air circulation means.

* * * * *